United States Patent [19]
West

[11] Patent Number: 5,172,683
[45] Date of Patent: Dec. 22, 1992

[54] STETHOSCOPE WARMER

[76] Inventor: Raymond O. West, P.O. Box 1137, Belfair, Wash. 98528

[21] Appl. No.: 835,300

[22] Filed: Feb. 12, 1992

Related U.S. Application Data

[63] Continuation-in-part of Ser. No. 624,405, Dec. 7, 1990, abandoned.

[51] Int. Cl.[5] ............................................. F24J 1/02
[52] U.S. Cl. .................................. 126/263; 181/141; 181/131; 181/126; 224/227; 224/252; 224/901
[58] Field of Search .................... 126/204, 206, 263; 128/402, 403, 715, 773; 181/126, 141, 131, 137; 381/67; 224/230, 252, 227, 901

[56] References Cited

U.S. PATENT DOCUMENTS

| 1,176,266 | 3/1916 | Batchelder | 224/227 |
|---|---|---|---|
| 3,167,875 | 2/1965 | Winner et al. | 126/204 |
| 3,213,960 | 10/1965 | Wagner | 181/126 |
| 3,476,102 | 11/1969 | Sarnoff | 126/204 |
| 3,766,361 | 10/1973 | Swinyon et al. | 219/521 |
| 3,793,643 | 2/1974 | Kinoshita | 126/204 X |
| 3,797,717 | 3/1974 | Collins | 224/230 X |
| 4,007,806 | 2/1977 | Nobles, Jr. | 181/131 |
| 4,573,447 | 3/1986 | Thrash et al. | 128/403 X |
| 4,705,086 | 11/1987 | O'Neil | 224/252 X |
| 4,742,755 | 5/1988 | Peterson | 84/453 |
| 4,867,268 | 9/1989 | Ulert | 181/137 |
| 4,972,832 | 11/1990 | Trapini et al. | 128/402 |

FOREIGN PATENT DOCUMENTS 0672412 11/1989 Switzerland ................. 128/715

Primary Examiner—Carl D. Price
Attorney, Agent, or Firm—Stetina and Brunda

[57] ABSTRACT

A portable stethoscope warming device incorporating an exothermic reaction heating element and adapted to be used with both diaphragm type and bell type stethoscopes. The device generally comprises a pouch member having a first pocket and a second pocket formed therein. The first pocket is adapted to receive either a diaphragm member or the bell member of conventionally known bell and diaphragm type stethoscopes. The second pocket is adapted to receive a heating element which comprises a packet having a bulkhead therein which, when ruptured, allows chemicals contained within the packet to mix in a manner producing a prolonged exothermic reaction. The second pocket is disposed directly adjacent the first pocket such that the heating packet is operable to warm the skin contacting surface of the diaphragm or bell member of the stethoscope.

10 Claims, 2 Drawing Sheets

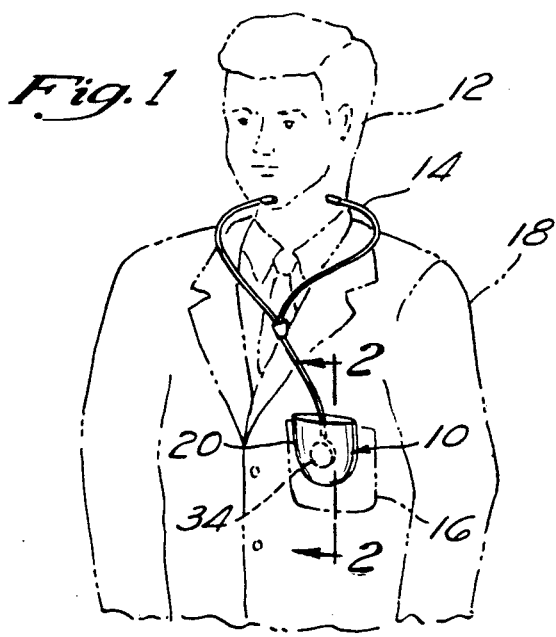
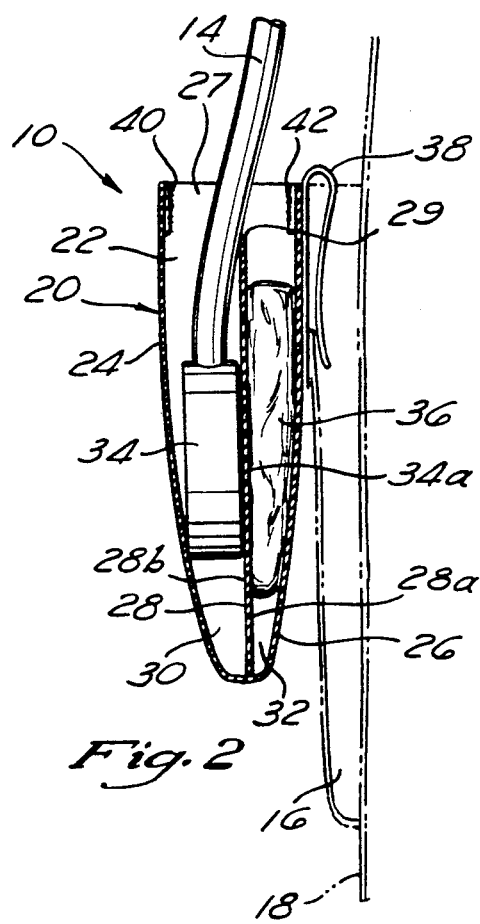
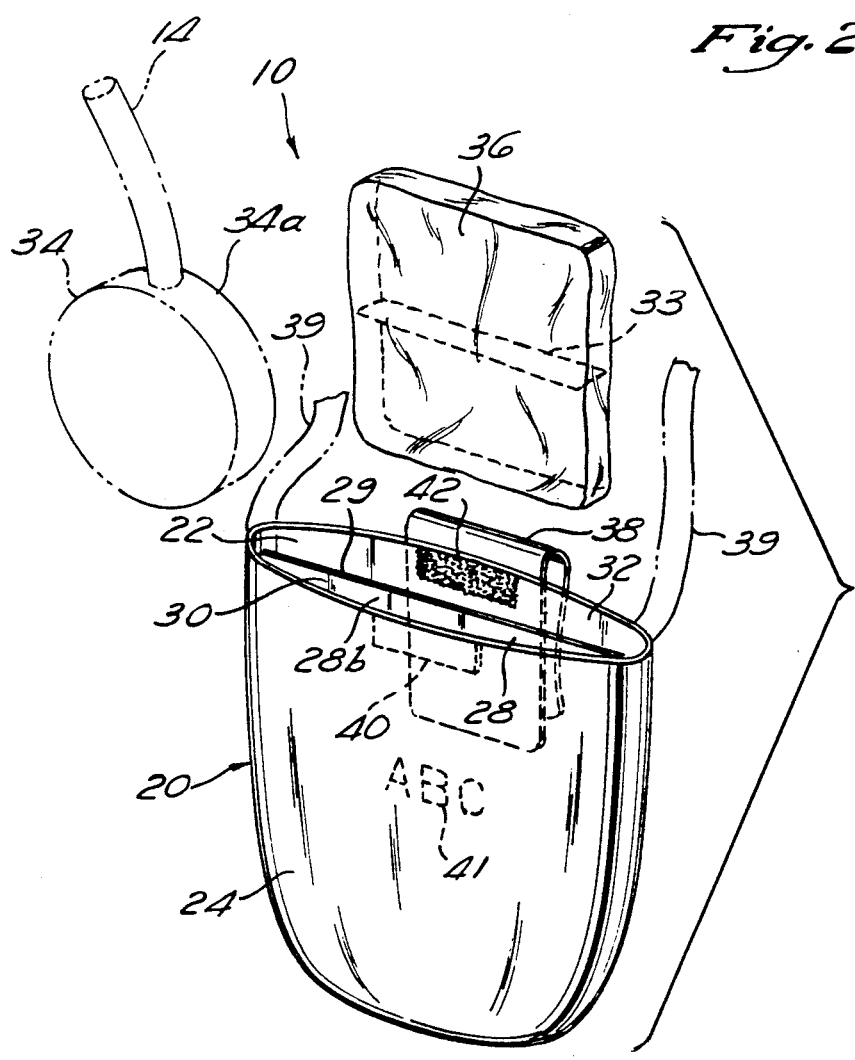

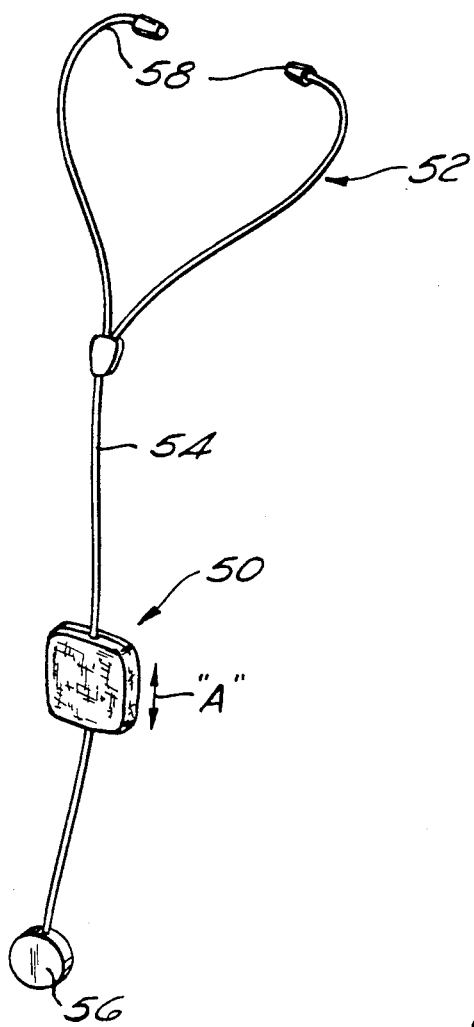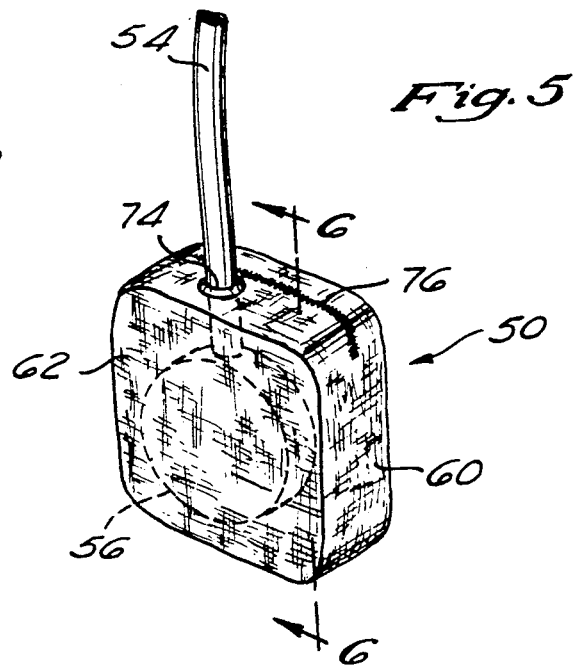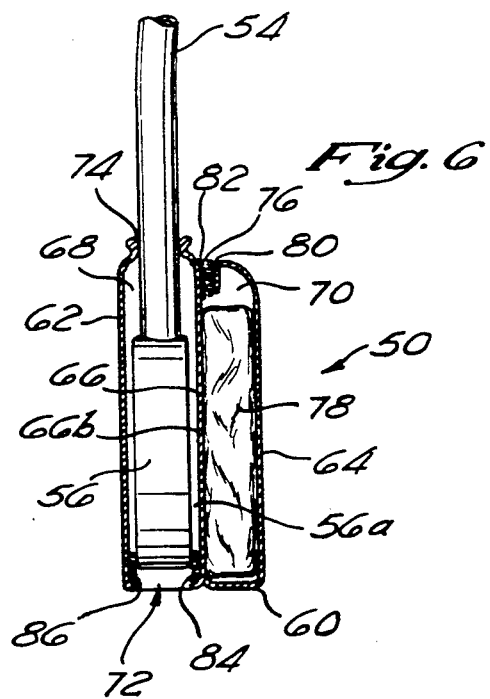

STETHOSCOPE WARMER

The present application is a continuation-in-part of application Ser. No. 07/624,405 filed Dec. 7, 1990, now abandoned.

FIELD OF THE INVENTION

The present invention relates generally to heating devices, and more particularly to a portable device for warming the sound conveying portion of a conventional stethoscope so as to reduce patient distress or trauma.

BACKGROUND OF THE INVENTION

Various types of stethoscopes (e.g. bell type, diaphragm type) are well known for purposes of conveying sounds from within a patient's body to a medical examiner during the examination of the patient. Currently, the diaphragm type of stethoscope is the most commonly used in the examination of both child and adult patients. As is well known, in using either a bell or diaphragm type stethoscope, the bell or diaphragm member thereof is placed on the warm skin of the chest, back or abdomen of the patient's body. A major problem associated with such stethoscopes results from the temperature of the bell or diaphragm member being lower than the temperature of the skin of the patient when the bell or diaphragm is pressed thereagainst. As can be appreciated, this temperature differential oftentimes causes distress in patients, especially children and infants, when auscultating the chest, back and abdomen. Particularly, the cold touch causes squirming, withdrawal or crying in infants and children and creates the possibility of tachycardia in susceptible adults.

Though a number of devices for providing warmed portions of stethoscopes are known in the prior art, such devices possess certain inherent deficiencies which detract from their overall utility. One such device is disclosed in U.S. Pat. No. 3,766,361 to Swinyar, et al. The device disclosed in this particular reference generally comprises an electrically heated hanger which is constructed to be hung on a nail or the like to a wall or other vertical support surface. The hanger is constructed in a manner so as to be usable only with diaphragm type stethoscopes and is provided with a pronged plug to electrically connect the heating element disposed in the hanger to a conventional electrical duplex wall socket. Thus, although the Swinyar, et al. device may be used to warm diaphragm type stethoscopes, the device is not portable and therefore is not readily usable by medical examiners during hospital rounds or other activities wherein such medical examiners are required to be in multiple locations.

A second device directed to providing a warmed stethoscope is disclosed in U.S. Pat. No. 4,007,806 to Nobles Jr. The Nobles Jr. device comprises a diaphragm type stethoscope having a heating element mounted within the head of the stethoscope substantially adjacent the diaphragm member. The device further includes a source of electrical power (i.e. a battery) which is fixedly attached to the head of the stethoscope in electrical communication with the heating element to selectively activate the heating element. Though Nobles Jr. addresses the problem of providing a warmed stethoscope diaphragm, this reference requires specially constructed stethoscopes to incorporate a heating element and power supply therein and hence, fails to allow retrofit to existing stethoscope constructions.

U.S. Pat. No. 3,213,960 to Wagner discloses a stethoscope head cover for insulating a stethoscope head from changes in temperature. However, the insulating cover disclosed in the reference merely insulates the stethoscope head from changes in temperature and will not prevent discomfort to the patient caused by the difference in the temperature between the stethoscope head and the patient's skin unless the head has been previously heated to a temperature corresponding to the temperature of the patient's body. Thus, there exists a need in the art for a stethoscope warming device which is portable, easy to construct and usable with more than one type of stethoscope.

SUMMARY OF THE INVENTION

In accordance with the preferred embodiment of the present invention, there is provided a portable device for warming the diaphragm or bell portion of a conventionally known stethoscope. The device generally comprises a pouch member having a wall member or partition disposed and secured within the pouch member in a manner forming a first pocket and a second pocket within the pouch member. In this respect, the wall member serves to separate the first pocket from the second pocket. In the preferred embodiment, the first pocket is sized and configured to receive the bell or diaphragm of the stethoscope while the second pocket is sized and configured to receive a heating element. Thus, the wall member is preferably constructed from a sheet of heat conducting material which is adapted to promote heat flow from the second pocket containing the heating element to the first pocket so as to maintain the bell or diaphragm at a desired temperature when such is inserted into the first pocket. The preferred heating element comprises a packet including a bulkhead therein which, when ruptured, is adapted to permit chemicals contained within the packet to mix in a manner producing a prolonged exothermic reaction. One such packet is disclosed in U.S. Pat. No. 4,649,895 and supplies a compact source of heat for up to twelve hours, however alternative exothermic reaction sources are contemplated herein. When the packet no longer produces heat, it is simply removed from the second pocket of the pouch member, and a new packet inserted in its place. Additionally, the pouch member is constructed from an insulating material which is adapted to maintain heat within the first pocket and second pocket. Thus, the present invention is utilized simply by having the medical examiner insert the bell or diaphragm of the stethoscope into the first pocket of the device prior to use of the stethoscope.

The pouch member of the present invention also includes a means for conveniently attaching the device to the medical examiner. The attaching means may comprise a clip member attached to an exterior surface of the pouch member which is adapted to be secured onto a pocket, belt, or other garment of the medical examiner. Alternatively, a cord may be connected to the outer surface of the pouch member in a manner whereby the cord may be placed around the neck of the medical examiner. The pouch member further includes a closure mechanism which is adapted to maintain the pouch (i.e. the first pocket and the second pocket) in a closed orientation when the bell or diaphragm of the stethoscope is not disposed within the first pocket. In he preferred embodiment, the closure mechanism comprises a Velcro fastener attached to the pouch member. Also it is contemplated that written or decorative indicia may be included on the outer surface of the pouch member to convey desired messages or to obtain desired aesthetic effects.

In accordance with a second embodiment of the present invention, the pouch member is formed to include an upper opening defining an entrance to the second pocket and an upper aperture and lower opening defining entrances to the first pocket. Importantly, the upper aperture is sized and configured to slidably receive the elongate, tubular portion of a stethoscope. In this respect, in utilizing the device constructed in accordance with the second embodiment, the tubular portion of the stethoscope is inserted through the upper aperture and first pocket with the sound conveying portion of the stethoscope being subsequently re-attached to the distal end of the tubular portion. Thereafter, the pouch member may be selectively slid downwardly along the tubular portion until the sound conveying portion is received into the lower opening and resides within the first pocket. Conversely, the pouch member may be slid upwardly along the tubular portion so as to remove the sound conveying portion from within the first pocket via the lower opening.

The device constructed in accordance with the second embodiment may further include a first fastener device for maintaining the upper opening in a closed orientation to retain the heating packet therewithin, and a second fastener device for maintaining the lower opening in a closed orientation to prevent the escape of heat or to prevent the sound conveying portion of the stethoscope from being received into the first pocket. In the second embodiment, the first and second fastener devices preferably comprise Velcro fasteners.

It is an object of the present invention to provide a stethoscope warming device which is portable and may be carried on the person of a medical examiner.

Another object of the present invention is to provide a stethoscope warming device suitable for retro-fitted use with both bell and diaphragm type stethoscopes.

Another object of the present invention is to provide a stethoscope warming device which includes a nonelectrical heating element.

A further object of the present invention is to provide a stethoscope warming device which is lightweight and easy to manufacture.

Further objects and advantages of the invention will become apparent to those skilled in the art upon reading and consideration of the following description of a preferred embodiment in the accompanying drawings.

BRIEF DESCRIPTION OF THE DRAWINGS

These as well as other features of the present invention will become more apparent upon reference to the drawings wherein:

FIG. 1 is a perspective view illustrating the manner in which the stethoscope warming device of the present invention is used by a medical examiner;

FIG. 2 is a cross sectional view taken along line 2—2 of FIG. 1;

FIG. 3 is an exploded view of the stethoscope warming device of the present invention, illustrating a diaphragm member of a diaphragm type stethoscope in phantom;

FIG. 4 is a perspective view of a stethoscope including a warming device constructed in accordance with a second embodiment of the present invention interfaced thereto;

FIG. 5 is a perspective view of the warming device of the second embodiment as interfaced to the sound conveying portion of the stethoscope; and FIG. 6 is a cross-sectional view taken along line 6—6 of FIG. 5.

DETAILED DESCRIPTION OF THE PREFERRED EMBODIMENT

Referring now the drawings wherein the showings are for purposes of illustrating a preferred embodiment of the present invention only and not for purposes of limiting the same, FIG. 1 perspectively illustrates a stethoscope warming device 10 constructed in accordance with the preferred embodiment of the present invention as used by a medical physician/examiner 12 (shown in phantom) to warm a conventional stethoscope 14. Although the following description will be directed toward diaphragm type stethoscopes, it will be appreciated that warming device 10 may also be used with bell type or other conventional type stethoscopes. As shown in FIG. 1, warming device 10 is secured to a pocket 16 attached to a lab coat 18 worn by examiner 12.

Referring now to FIGS. 2 and 3, warming device 10 generally comprises a pouch member 20 defining an interior chamber 22 and having an outer surface 24 and an inner surface 26. Defining the entrance to interior chamber 22 is an opening 27. Disposed within interior chamber 22 of pouch member 20 is a wall member or partition 28 defining an upper edge 29. As best seen in FIG. 2, wall member 28 is secured within interior chamber 22 in a manner forming a first pocket 30 and second pocket 32 within pouch member 20. As seen in FIG. 2, wall member 28 is sized and configured so as to substantially bisect interior chamber 22 such that the first pocket 30 and second pocket 32 are substantially the same size. However, first pocket 30 and second pocket 32 need not necessarily be of equal size in order for warming device 10 to function properly. Additionally, wall member 28 is preferably sized such that the upper edge 29 thereof resides within interior chamber 22 slightly below opening 27, for reasons which will be explained below.

In the preferred embodiment of the present invention, first pocket 30 is sized and configured to receive a diaphragm member 34 of stethoscope 14 via opening 27. First pocket 30 may also receive a bell member (not shown) of a bell type stethoscope. Disposed within second pocket 32 is a heating element 36. In the preferred embodiment, heating element 36 comprises a packet having a bulkhead 33 therein which, when ruptured, is adapted to permit chemicals contained within heating element 36 to mix in a manner producing a prolonged exothermic reaction. Such a heating element 36 is described in U.S. Pat. No. 4,649,895 and currently sold under the trademark "HEAT FACTORY" although alternative substitute exothermic reaction heating elements are contemplated herein. Advantageously, heating element 36 is adapted to supply a prolonged source of heat lasting for up to twelve hours. Heating element 36 is disposed within the second pocket 32 in a manner wherein a substantial portion of heating element 36 is directly abutted against the inner surface 28a of wall member 28. Wall member 28 is preferably constructed from a sheet of heat conducting material which is operable to rapidly transmit heat from heating element 36 within second pocket 32 to first pocket 30. Diaphragm member, i.e. the sound conveying portion, 34 of stethoscope 14 is inserted into first pocket 30 in a manner whereby the skin contacting surface 34a of diaphragm member 34 is directly abutted against the outer surface 28b of wall member 28. As can be appreciated, disposing diaphragm member 34 within first pocket 30 in this manner optimizes the heat transfer from heating element 36 to the skin contacting surface 34a of diaphragm member 34. After the heat generating capacity of heating element 36 has been exhausted, heating element 36 is removed from second pocket 32 and a new packet is manipulated to rupture the bulkhead therein to initiate the exothermic reaction with the packet then being inserted in its place within the second pocket. Since heating element 36 has a heat generating capacity of approximately twelve hours, one such heat packet is generally suitable for use during normal hospital rounds of a physician or other medical examiner. It will be appreciated that pouch member 20 may be constructed from inexpensive materials and that heating element 36 may be integrally connected to pouch member 20 such that the entire warming device 10 is disposed of after heating element 36 has become exhausted.

Pouch member 20 is preferably fabricated from a soft, flexible insulating material which is operable to prevent heat from escaping either first pocket 30 or second pocket 32. Examples of such materials include leather and vinyl though it will be appreciated that other thermally insulating materials may be utilized. The pouch member 20 preferably has a height of approximately 2" and a length of approximately 3". Attached to inner surface 26 of pouch member 20 is a clip 38. Clip 38 may be used to attach pouch member 20 to the pocket 16 of a lab coat 18 as shown, or a belt (not shown) of the medical examiner in a manner substantially identical to that as accomplished by the clip on a spectacle case. As an alterative to clip 38, a cord 39 (partially shown in phantom in FIG. 3) may be connected to pouch member 20 in a manner such that the cord may be placed around the neck of a medical examiner. Additionally, pouch member 20 may be provided with a strap member which may be wrapped around the waist of the medical examiner. It is further contemplated that pouch member 20 may include a magnet or piece of Velcro attached thereto for securing pouch member 20 to a medical examining table or instrument stand.

It will be appreciated that inserting heating element 36 into first pocket 30 and inserting diaphragm member 34 into second pocket 32 will achieve the same results as previously specified. It is further contemplated that written or decorative indicia 41 may be disposed on outer surface 24 of pouch member 20 for purposes of either conveying a written message or for providing certain aesthetic effects. Disposed within interior chamber 22 adjacent the opening 27, are fastening members 40, 42 which are used to maintain pouch member 20 in a closed configuration when diaphragm member 34 of stethoscope 12 is not inserted within first pocket 30. In this respect, fastening member 40, 42 are operable to maintain heat within first pocket 30 and second pocket 32 thereby prolonging the useful life of heating element 36. Importantly, due to the size of wall member 28 the fastening members 40, 42 are not interfered with thereby. In the preferred embodiment, fastening members 40, 42 comprise Velcro straps, though it will be appreciated that other devices (i.e. snaps, zippers) may be utilized as an alternative.

Referring now to FIGS. 4–6, disclosed is a stethoscope warming device 50 constructed in accordance with a second embodiment of the present invention. In the second embodiment, warming device 50 is adapted to be interfaced directly to a stethoscope 52, and more particularly the elongate tubular portion 54 thereof lying between the sound conveying portion 56 and ear portions 58. It will be recognized that though sound conveying portion 56 of stethoscope 52 as hereinafter described is of the diaphragm variety and the warming device 50 configured to receive the same, the warming device 50 may be alternatively configured to be used in conjunction with differently configured sound conveying portions of stethoscopes such as a bell type.

Similar to the warming device 10 previously described, the warming device 50 comprises a pouch member 60 defining an interior chamber and having an outer surface 62 and an inner surface 64. Disposed within the interior chamber of pouch member 60 is a wall member 66 which completely, or at least substantially, bisects the interior chamber in a manner forming a first pocket 68 and a second pocket 70 which are directly adjacent one another. The pouch member 60 further includes a lower opening 72 defining a first entrance to first pocket 68, an upper aperture 74 defining a second entrance to first pocket 68, and an upper opening 76 defining an entrance to second pocket 70. In the second embodiment, upper aperture 74 is sized and configured to slidably receive the tubular portion 54 of stethoscope 52 for reasons which will be discussed in greater detail below.

In the second embodiment, first pocket 68 is sized and configured to receive the sound conveying portion 56 of stethoscope 52 via lower opening 72 which is sized and configured to receive the same. Disposed within second pocket 70 is a heating element 78 identical to the heating element 36 previously described with respect to the first embodiment. In this respect, upper opening 76 is sized and configured to facilitate the insertion of heating element 78 into second pocket 70. As in the first embodiment, the wall member 66 of the second embodiment is also preferably constructed from a sheet of heat conducting material which is operable to rapidly transmit heat from heating element 78 within second pocket 72 to first pocket 68. As such, the sound conveying portion 56 of stethoscope 52 is preferably inserted into first pocket 68 in a manner whereby the skin contacting surface 56a of sound conveying portion 56 is directly abutted against the outer surface 66b of wall member 66.

In utilizing the warming device 50 constructed in accordance with the second embodiment, initially the sound conveying portion 56 of the stethoscope 52 is removed such that the tubular portion 54 may be inserted initially through the upper aperture 74 and subsequently through the first pocket 68. Thereafter, the sound conveying portion 56 is re-attached to the tubular portion 54 of stethoscope 52. As will be recognized, due to the sizing of upper aperture 74, the warming device 50 may be freely slid axially along the length of tubular portion 54 as designated by the arrow "A" shown in FIG. 4. During utilization of the warming device 50, a heating element 78, identical to heating element 36, is manipulated in the manner previously described and inserted into the second pocket 70 via upper opening 76. When it is desired to warm the skin contacting surface 56a of sound conveying portion 56, the warming device 50 is slid axially downwardly along tubular portion 54 such that the sound conveying portion 56 is received into first pocket 68 via lower opening 72. When the sound conveying portion 56 is to be utilized, the warming device 50 is slid axially upwardly along the tubular portion 54 thereby removing the sound conveying portion 56 from within the first pocket 68. In the second embodiment, pouch member 60, like pouch member 20, is also preferably fabricated from a soft, flexible insulating material such as leather or vinyl which is operable to prevent heat from escaping from within first pocket 68 and second pocket 70.

As best seen in FIG. 6, the warming device 50 of the second embodiment may include fastening members 80, 82 for maintaining upper opening 76 in a closed configuration. In the second embodiment, fastening members 80, 82 comprise Velcro straps, though it will be appreciated that other devices (i.e. snaps, zippers) may be utilized as an alternative. The fastening members 80, 82 are preferably disposed within second pocket 70 immediately adjacent upper opening 76 and are operable to maintain heat within second pocket 70 as well as retain heating element 78 therewithin. Additionally, disposed within first pocket 68 immediately adjacent lower opening 72 are fastening members 84, 86 which are used to close lower opening 72 about the tubular portion 54 of stethoscope 52. In this respect, such closure serves to not only maintain heat within first pocket 68, but also serves to block the entrance of the sound conveying portion 56 into first pocket 68. Advantageously, the use of the fastening members 80, 82 and/or fastening members 84, 86 prolongs the useful life of the heating element 78.

Additional modifications and improvements of the invention may also be apparent to those skilled in the art. Thus, the particular combination of parts described and illustrated herein is intended to represent only one embodiment of the invention and is not intended to serve as limitations of alterative devices within the spirit and scope of the invention.

What is claimed is:

1. A portable device for warming a sound conveying portion of a stethoscope comprising:
    a pouch member defining an interior chamber, a lower opening defining a first entrance to said interior chamber, an upper opening defining a second entrance to said interior chamber, and an upper aperture defining a third entrance to said interior chamber, said upper aperture being sized and configured to slidably receive a tubular portion of said stethoscope;
    a wall member disposed within said interior chamber, said wall member being sized and configured so as to substantially bisect said interior chamber in a manner forming first and second adjacent pockets therein, said first pocket being sized and configured to receive said sound conveying portion of said stethoscope, said upper aperture and said lower opening defining entrances to said first pocket and said upper opening defining an entrance to said second pocket; and
    a heating means disposed within said second pocket for heating said sound conveying portion of said stethoscope when said sound conveying portion is disposed within said first pocket.

2. The device of claim 1 wherein said heating means comprises;
    a packet insertable into said second pocket via said upper opening, said packet including a bulkhead therein which, when ruptured, is adapted to permit chemicals contained within said packet to mix in a manner producing a prolonged exothermic reaction.

3. The device of claim 2 wherein said wall member comprises a sheet of heat conducting material adapted to permit heat to flow from said packet disposed in said second pocket to said first pocket.

4. The device of claim 3 wherein said pouch member is constructed from an insulating material adapted to maintain heat within said first pocket and said second pocket.

5. The device of claim 1 wherein said pouch member includes written indicia thereon.

6. The device of claim 1 wherein said pouch member includes decorative indicia thereon.

7. The device of claim 1 further including a fastening device for maintaining said upper opening in a closed configuration.

8. The device of claim 7 wherein said fastening device comprises a Velcro fastener disposed within said second pocket adjacent said upper opening.

9. The device of claim 1 further including a second fastening device for maintaining said lower opening in a closed configuration when said sound conveying portion of said stethoscope is not disposed within said first pocket.

10. The device of claim 9 wherein said fastening device comprises a Velcro fastener disposed within said first pocket adjacent said lower opening.

* * * * *